(12) United States Patent
Bosselmann et al.

(10) Patent No.: US 6,470,205 B2
(45) Date of Patent: Oct. 22, 2002

(54) MEDICAL INSTRUMENT FOR INSERTION INTO AN EXAMINATION SUBJECT, AND MEDICAL EXAMINATION/TREATMENT DEVICE EMPLOYING SAME

(75) Inventors: Thomas Bosselmann, Marloffstein (DE); Oliver Schuetz, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 50 days.

(21) Appl. No.: 09/804,804

(22) Filed: Mar. 13, 2001

(65) Prior Publication Data

US 2001/0021843 A1 Sep. 13, 2001

(30) Foreign Application Priority Data

Mar. 13, 2000 (DE) .......................................... 100 11 790

(51) Int. Cl.7 ............................. A61B 5/05; A61B 18/18
(52) U.S. Cl. ......................................... 600/424; 606/15
(58) Field of Search ................................ 600/407, 424, 600/310, 431, 427, 429, 109, 114; 606/2, 15, 17, 148; 356/72; 385/12; 359/22, 34, 15

(56) References Cited

U.S. PATENT DOCUMENTS 5,014,709 A * 5/1991 Bjelkhagen et al. ........ 600/431
5,104,392 A    4/1992 Kittrel et al.
6,066,130 A    5/2000 Gregory et al.
6,088,088 A    7/2000 Fortenberry
6,398,778 B1 * 6/2002 Gu et al. ..................... 606/15

FOREIGN PATENT DOCUMENTS

| DE | 196 29 530 | 10/1997 |
| DE | 196 21 112 | 11/1997 |
| DE | 198 27 258 | 12/1999 |
| DE | 199 11 182 | 9/2000 |
| DE | 199 22 102 | 12/2000 |
| DE | 199 62 668 | 12/2000 |

* cited by examiner

Primary Examiner—Tu Ba Hoang
(74) Attorney, Agent, or Firm—Schiff Hardin & Waite

(57) ABSTRACT

In a medical instrument for insertion into an examination subject, as well as a medical examination device or treatment device employing such an instrument, the instrument has an elongated instrument body formed by a number of successively arranged rigid sections, with respective, successive sections being connected to one another via articulated joints which can be angled relative to one another. At least one optical fiber supplied with light is conducted along the instrument body, and at least one fiber Bragg grating is fashioned in the optical fiber in a region adjacent to a joint which is deformed to a degree corresponding to angling of the adjacent sections to the joint, thereby modulating the light in the optical fiber.

62 Claims, 2 Drawing Sheets

MEDICAL INSTRUMENT FOR INSERTION INTO AN EXAMINATION SUBJECT, AND MEDICAL EXAMINATION/TREATMENT DEVICE EMPLOYING SAME

BACKGROUND OF THE INVENTION

1. Field of the Invention

The present invention relates to a medical device for insertion into an examination subject of the type having an elongated instrument body with a number of serially arranged rigid sections, respectively connected to one another via articulated joints so that the sections can be angled relative to one another.

2. Description of the Prior Art

Instruments of the above type can be catheters or endoscopes, for example. Using such an instrument it is possible to enter into the inside of the body of a patient via a very small body opening and to carry out different surgical measures. The instrument can be manually guided or automatically guided or by a robot. Since the instrument is no longer visible after it has been inserted into the body, it is necessary to exactly determine its position during the intervention in the patient and to fade the position information into preoperative or intraoperative patient images, so that the treating physician exactly knows where the instrument, and particularly the tip of the instrument, is situated. Conventionally, the positioning currently ensues using X-ray control, which normally makes only one projection direction available. For detecting the position, it is also known to use electromagnetic navigation systems, wherein sensor coils are integrated into the instrument tip. The sensor coils are localized via an external detection system in a coordinate system of the navigation system and are faded into previously obtained patient images after a coordinate transformation has been carried out. These known methods, however, have disadvantages. The radiation load on the patient is considerable during the determination of the position with X-ray control, and the determination of the position is quite difficult. The electromagnetic navigation system is susceptible to electromagnetic radiation and cannot be used in connection with other medical examination devices such as X-ray apparatuses, computed tomography devices or magnetic resonance apparatuses.

SUMMARY OF THE INVENTION

An object of the invention is to provide a medical instrument whose position in a subject body can be simply determined.

This object is inventively achieved in a medical instrument of the initially described type wherein at least one optical fiber that can be charged with light is conducted along the instrument body, with at least one fiber Bragg grating fashioned in a region adjacent each articulated joint.

An extremely accurately operating optical navigation system is realized by the optical fiber having at least one integrated fiber Bragg grating in the inventive instrument. A fiber Bragg grating is characterized by changing areas having different refractive indices. Such a grating acts as a wavelength-sensitive mirror having an extremely high reflective factor up to 99% and a half intensity width of below 0.05 nm. If light having a finite half intensity width is radiated through the optical fiber onto the fiber Bragg grating, a discrete, exactly defined wavelength of the light differing from the grating constant and the average effective refractive index of the grating is reflected back. If the joint position of the instrument is modified, a bending of the optical fiber and therefore of the fiber Bragg grating is also associated therewith, which causes an associated change of the reflective behavior and therefore of the reflected Bragg wavelength. As a result of this modification that can be detected by a suitable detection unit, or on the basis of the reflected wavelength modified as a result of the bending, the joint position can be extremely precisely determined in a particularly advantageous way. Since optical fibers are produced with diameters smaller than 100 $\mu$m, ths system therefore is extremely light and compact, and is advantageously insusceptible to electromagnetic radiation and therefore can be utilized in cooperation with other medical devices such as X-ray apparatuses, computed tomography apparatuses or magnetic resonance apparatuses. Since only the wavelength of the back-reflected light is important for determining the joint position, changes in intensity or polarization, which may be influenced by a dynamic conductor bending, therefore also have no effect on the measurement result. Overall, the inventive instrument enables the exact determination of the joint position with an extremely simple and compact structure and avoids the disadvantages of known devices.

In a further embodiment of the invention, a number of fiber Bragg gratings that are respectively allocated to the articulated joints are provided along the length of the optical fiber, each of these fiber Bragg gratings reflecting light of a grating specific wavelength range, the wavelength ranges of all fiber Bragg gratings of a optical fiber being different. Normally, a number of articulated joints are provided over the length of the instrument. In this embodiment, each articulated joint has a separate grating allocated thereto, which reflects in a specific wavelength range, so that the reflected light can be unambiguously allocated to a specific grating and therefore to a specific joint. For an unbent waveguide, the wavelength difference of the reflected light of two successively arranged gratings should be at least double the half intensity width of the grating reflected light of a single grating, particularly at least 1 nm. The reflected wavelength can be adjusted without a problem by correspondingly fashioning the grating. Each reflected light beam, therefore each Bragg peak, has a specific width that is determined by the formation of the grating. The difference should correspond to at least double the half intensity width of these Bragg peaks. The double of the half intensity width is normally situated between 100–200 pm. This difference value represents the lower limit. A difference of at least 1 nm is preferred in order to obtain a sufficient safety margin. The cited wavelength difference is sufficient with regard to the modification of the reflected wavelength of a grating between the extremes "maximal contraction" and "maximal expansion", since the wavelength normally changes by less than 1 nm.

The articulated joints can be normally rotated around two orthogonal axes. In order to enable an exact determination of the position, it is expedient in this case when at least two optical fibers are provided, which are arranged at the instrument body at respective positions that are offset by 90°, and which each have a fiber Bragg grating fashioned at the regions adjacent to an articulated joint. Each of the two joint-related gratings supplies a specific signal dependent on the direction of the joint bending, so that the bend angle can be exactly calculated on the basis of the supplied signals.

In a further embodiment, four optical fibers can be provided, which are arranged at the instrument body at positions that are offset by 90°, and which each have at least one fiber Bragg grating fashioned at the regions adjacent to a link joint. This embodiment makes it possible to measure the difference between two opposite gratings. For example, if the joint is bent around an axis, the one grating is stretched and the other grating is compressed. On this basis, it can be recognized that a bend actually occurs in this case around this axis. Due to the bending, the two other gratings, which, as it were, are situated on the rotational axis, are also somewhat bent, but uniformly, so that both supply positive or negative signals. On the basis thereof, it can be unambiguously recognized that these two gratings do not experience a bending that is relevant for an angle modification, but they are merely bent together. It is thus possible to exactly determine the bending direction, particularly in the case of ball-and-socket joints.

A modification of the reflected wavelength can also be caused by temperature. Given increased temperature, the optical fiber expands and therefore the grating expands somewhat as well, whereas it somewhat contracts at a low temperature. The grating constant changes somewhat as a result, and the reflected light wavelength is dependent thereon. Since a temperature jump occurs when the instrument is inserted into the patient body, normally being 37° C. compared to the room temperature, it is necessary to carry out a temperature compensation. For this purpose, a further fiber Bragg grating, which at least serves the purpose of compensating the temperature, can be fashioned at at least one optical fiber in an unmovable region of the optical fiber, which is not moved given a bending. Preferably, a fiber Bragg grating for this purpose should be allocated to each joint. These further gratings therefore supply temperature-dependent signals on the basis of which it is possible to compensate the temperature-caused modification of the reflected light wavelength of the actual gratings serving for measuring the bending. The arrangement of a further grating in the area of the link joint is advantageous, since the temperature jump is particularly relevant when a joint has just been inserted into the patient from the exterior. For example, if the temperature grating is arranged only at the tip of the instrument, which has already been in the warm interior of the body for a while, an erroneous correction possibly would occur. The temperature-caused change in wavelength is significantly smaller than the change which occurs due to mechanical bending. As a result, small wavelength differences between the gratings situated in the area of the cited lower limit are sufficient.

The fiber Bragg gratings should be sensitive to wavelengths in the range between 750 nm to 850 nm, 1250 nm to 1350 nm or 1500 to 1600 nm.

In addition to the instrument itself, the invention also relates to a medical examination device or treatment device, having an inventive medical instrument of the above-described type, and a light source at which the optical fiber or the optical fibers of the medical instrument are coupled or can be coupled via an optical coupling element, at least one detection unit that is coupled or can be coupled to the optical fiber or optical fibers for detecting the wavelength of the light reflected from the fiber Bragg grating or the fiber Bragg gratings, and a computing unit for determining the angle position of the sections relative to one another, and the spatial position of the medical instrument, on the basis of the detected wavelengths.

The medical instrument can be firmly coupled to the light source or can be detachably coupled via a simple optical plug connection. This is also true for the detection unit, which detects the wavelengths of the reflected light and forwards the detected result to the computing unit for resolving the angle positions. A spectrometer or an interferometer can be utilized as the detection unit.

The light source should be capable of emitting light having a spectral bandwidth of 10 nm to 60 nm. The wavelength of the emitted light should be situated in the ranges between 750 nm to 850 nm, 1250 nm to 1350 nm or 1500 to 1600 nm. It is expedient when a number of light sources are provided, which emit in different wavelength ranges in order to be able to couple different instruments, whose gratings reflect in the different wavelength ranges, so that a universally utilizable device is given. The detection unit and the computing unit can be fashioned in order to operate with the different reflected wavelengths. The light source itself can be a variable frequency laser diode or a LED.

In a further embodiment of the invention, at least one reference optical fiber can be provided, which supplies reference reflection light and which has at least one fiber Bragg grating, which can be charged with the light of the light source and which is coupled or can be coupled to its own detection unit or to the aforementioned detection unit. The reference reflection light serves for calibrating purposes in order to calibrate the device with respect to a standard. The reference optical fiber is also coupled, or can be coupled, to the light source via a suitable optical coupling element, as is also true for coupling to the detection unit.

Furthermore, the inventive device can have a display unit in the form of a monitor at which the spatial position of the medical instrument can be displayed in an image of an area of the examination subject, this image being shown at the display device. Therefore, the computing device is capable of mixing the instrument, which is determined regarding its spatial position, into an earlier or simultaneously obtained patient image correctly in terms of position. For this purpose, it is necessary to transform the coordinates of the medical instrument, which are determined in a first coordinate system of the optical navigation system, into the coordinate system, which is based on the patient image, in a calculated fashion.

The invention also relates to an optical navigation system for determining the spatial position of an operating instrument, which is composed of a number of successively arranged segments that are flexibly connected via articulated joints, having at least one optical fiber, which is conducted along the operating instrument and which is charged with light, with at least one fiber Bragg grating in a region adjacent to an articulated joint. The navigation system also has a light source, at which the optical fiber or optical fibers of the operating instrument are coupled or can be coupled via an optical coupling element. The navigation system has at least one detection unit that is coupled or can be coupled to the optical fiber or optical fibers for detecting the wavelength of the light reflected from the fiber Bragg grating or the fiber Bragg gratings, and a computing unit for determining the angle position of the sections to one another and the spatial position of the medical instrument on the basis of the detected wavelengths.

DESCRIPTION OF THE PREFERRED EMBODIMENTS

Figure 1:
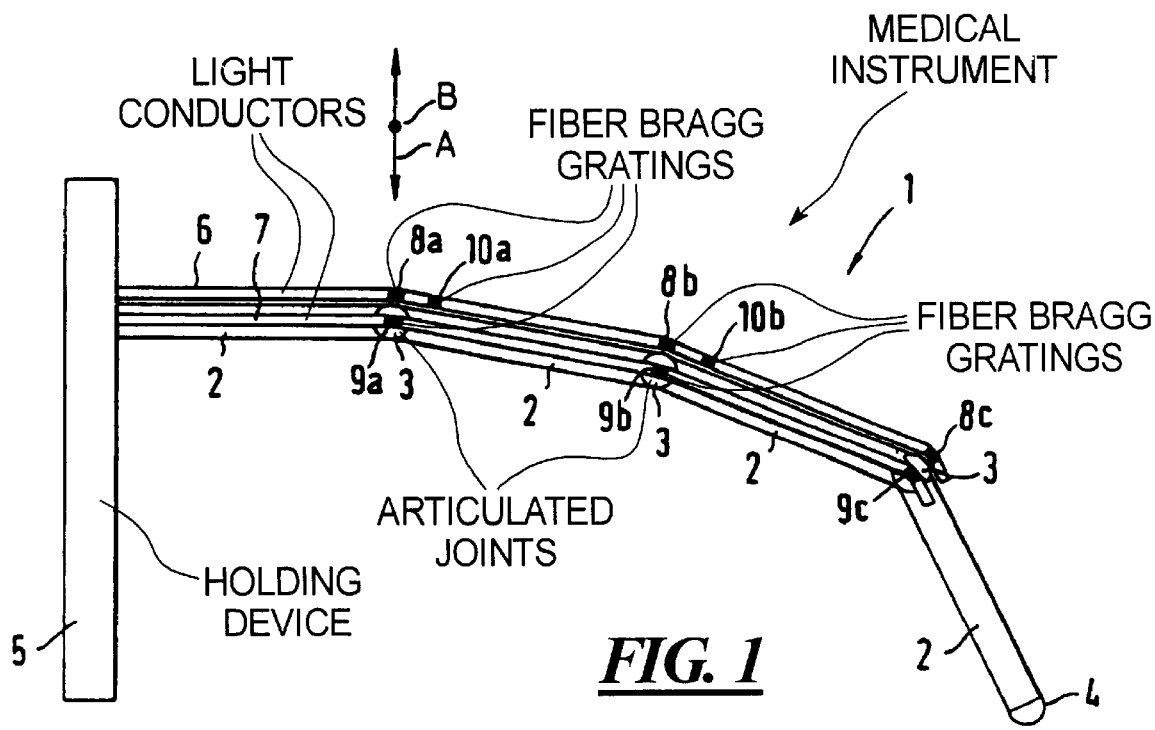
FIG. 1 is a schematic illustration of an inventive medical instrument in a first embodiment.

FIG. 1 schematically shows an inventive medical instrument 1 in a first embodiment. It is composed of a number of rigid sections 2, which are successively coupled via articulated joints 3. In the shown example, the joints can be moved around two rotational axes namely axis A, which is situated in the plane of the drawing, and axis B, which is situated perpendicular to the plane of the drawing. This movability makes it possible to place the instrument 1 at an arbitrary position and to arbitrarily position the tip of the instrument 4. The instrument 1 can be a catheter or an endoscope, for example. In the shown example, the instrument 1 is fashioned in the nature of a robot arm, which is arranged at a holding device 5. Alternatively, the instrument can be fashioned as an instrument to be manually guided.

Two optical fibers 6, 7, which are offset at an angle of 90° relative to one another, are conducted along the instrument body formed by the sections 2. The optical fibers 6, 7 are firmly arranged and are co-moved when a section 2 is moved. Fiber Bragg gratings 8a, 8b, 8c and 9a, 9b, 9c are fashioned in the optical fibers 6, 7 in the conductor sections adjacent to the respective joints 3. These gratings can be fashioned in doped optical fibers by illumination with UV light. They consist of alternating areas having of different refractive indices. In the formation of the gratings, the fact is utilized that the core refractive index increases as a result of the radiation with ultraviolet light. Alternatively, the gratings can be generated by interference with two laser beams. The gratings act as a wavelength-selective reflecting mirror that reflect light of a specific grating-specific wavelength that is irradiated into the respective optical fiber. The wavelength of the light depends on the grating constant and therefore depends on the distance of the regions having different refractive indexes and on the average effective refractive index of the grating. The gratings 8a–8c, 9a–9c successively following in a conductor in the shown example are fashioned such that each grating is selective for a different wavelength and therefore reflects light of a different wavelength back.

Furthermore, two further fiber Bragg gratings 10a, 10b are provided in the optical fiber 6, these two fiber Bragg gratings 10a, 10b being arranged in an area which is close to the joint but which is not deformed given a movement of two sections relative to one another. These serve the purpose of compensating the temperature, they also reflect light of a specific wavelength.

If two sections are now angled relative to one another, the respective optical fiber follows the angle—i.e., mechanical stress arising from the bending is introduced into the fiber Bragg grating. This stress leads to a stretching or compression of the grating. The grating constant changes as a result, so that the wavelength of the reflected light changes. The change in wavelength is greater the more the grating is deformed. In this way, it can be determined with respect to a specific wavelength of the reflected light how intense the introduced mechanical stress is and therefore the angle position of the sections relative to one another can be determined. It is thereby possible to change the wavelength of the reflected light between the two extreme positions "maximal compression" or "maximal expansion". The reflected wavelength also correspondingly changes given a thermal change, since the grating constant also changes as a result of expansion given a higher temperature or a contraction given a lower temperature. The reflected wavelength also changes with regard to temperature, so that an unambiguous statement about the existing local temperature is possible with respect to a given wavelength. The further Bragg gratings 10a, 10b serve the purpose of determining possible temperature fluctuations in order to compensate resulting wavelength changes, which occur in the adjacent gratings 8a–8c, 9a–9c in the same way.

Figure 3:
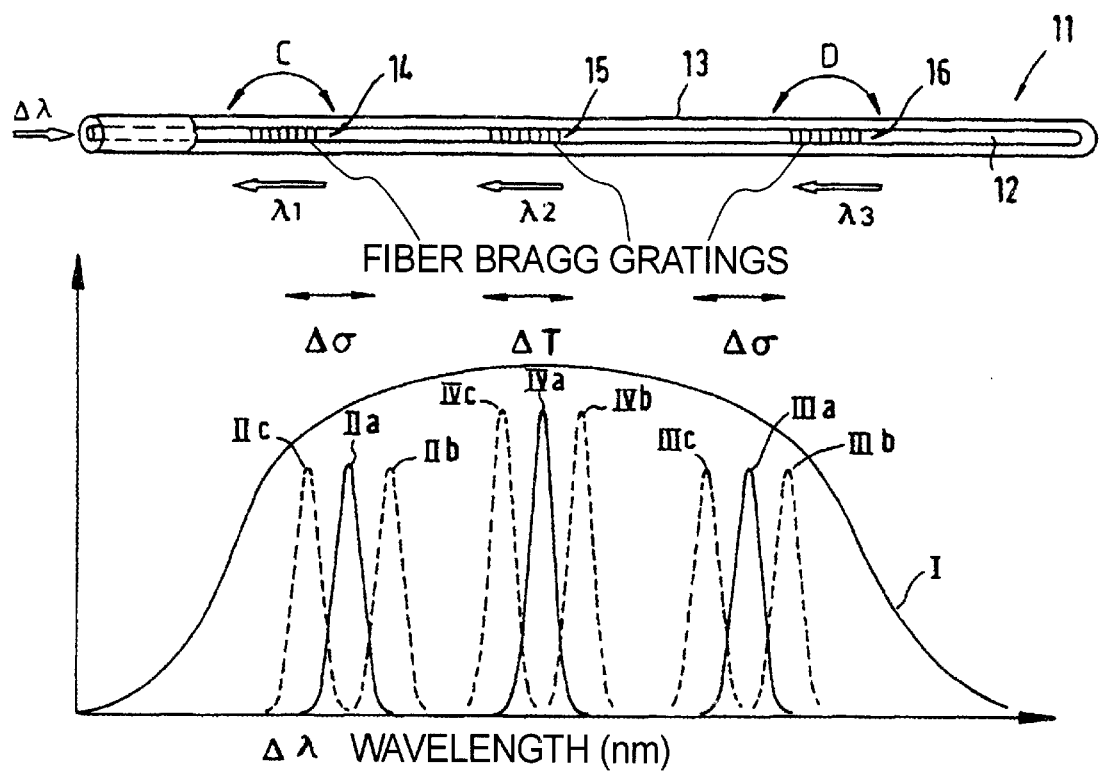
FIG. 3 is a schematic diagram for representing the function of the fiber-Bragg grating given mechanical and thermal stress.

FIG. 3 shows the principle in detail. In the upper diagram, a optical fiber 11 is schematically shown, which is composed of a wave-guiding core 12 and a jacket 13, which have different refractive indices. In the shown example, three fiber Bragg gratings 14, 15, 16 are fashioned in the core 12. These areas, having different refractive indices are indicated by lines. In the shown example, the gratings 14, 16 are provided for acquiring possible bending (indicated by the two double arrows C, D). The bending can be upward or downward. Since the optical fiber extends at the outer side of the instrument body, the bending in one direction effects an expansion of the grating and effects a compression of the grating in the other direction. The middle grating 15 is provided for determining temperature fluctuations.

As shown, the gratings 14, 15, 16 are designed for different reflected wavelengths $\lambda 1, \lambda 2, \lambda 3$. For example, the grating 14 reflects light of the wavelength 815 nm in an unbent (non-deformed) state, the grating 15 reflects the wavelength 820 nm and the grating 16 reflects the wavelength 825 nm.

In the lower graphic, FIG. 3 shows the effects of a deformation or thermal change given irradiation of a light of the wavelength bandwidth $\Delta\lambda$. The bell-shaped curve I shows a light spectrum of the irradiated light $\Delta\lambda$. The bandwidth $\Delta\lambda$ should be between 10 nm and 60 nm. The curves IIa, IIb, IIc represent the reflected light of the grating 14. In an unbent state, light is reflected according to curve IIa, for example with the indicated wavelength 815 nm. If the grating 14 is deformed such that it is stretched, (expanded) the grating constant increases, so that the reflected light wavelength becomes larger—light is then reflected according to curve IIb. In the case of a compressing, the grating constant decreases, so that the reflected light wavelength is lowered according to the curve IIc. Assuming that the curves IIb and IIc represent the two maximal bendings, each intermediate position can be described on the basis of a discrete reflected light wavelength lying within the wavelength region that is defined by the curves IIb, IIc. The reflected light of the grating 16 shows a corresponding behavior—merely displaced toward higher wavelengths (see curves IIIa, IIIb, IIIc).

Thermal influences also cause the described changes of the grating constant, and this can also be seen in a change of the reflected light wavelength (as shown in the curves IVa, IVb, IVc). For a given room temperature, the grating reflects the basic reflective wavelength according to curve IVa, therefore 820 nm, for example. Given a temperature rise and therefore enlargement of the grating constant, the reflective light wavelength becomes greater, and it becomes smaller when the temperature is lower. The wavelength change can be unambiguously allocated to the temperature change.

All gratings 8a–8c, 9a–9c, 10a, 10b of the optical fibers 6, 7 of the instrument 1 as shown in FIG. 1 have a behavior following the principle as shown in FIG. 3. Since the opposite gratings 8a–8c, 9a–9c pick up signals in the area of a joint 3 at the same time, and since the gratings are exactly situated in the respective rotational axes A, B, it is possible to unambiguously determine the respective angle and the respective pivot axis on the basis of the received signals. In this way, the spatial position between two sections can be exactly determined.

Figure 2:
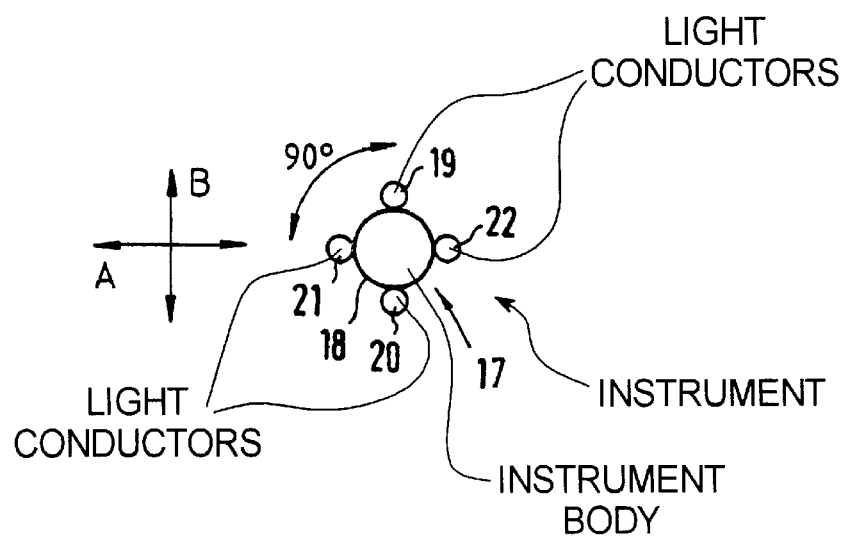
FIG. 2 is a schematic illustration in section of an inventive medical instrument of a second exemplary embodiment.

FIG. 2 shows another embodiment of an inventive instrument 17. Four optical fibers 19, 20, 21, 22, which are respectively distanced by 90°, are fastened at the instrument body 18. Two oppositely situated conductors 19, 20 or 21, 22, lie in the respective rotational axis A and B. If the instrument at the joint is now angled around the axis A, the optical fiber 19 is expanded, for example, whereas the conductor 20 situated at the opposite side is compressed. This has the effect that an increased reflected light wavelength is measured at the upper conductor 19, and a lowered reflective light wavelength is measured at the lower conductor 20, thereby respectively producing a positive signal and a negative signal. It can be unambiguously determined therefrom that a movement around this axis has actually occurred.

The two conductors 20, 21 are also somewhat deformed during the angling, but in the same direction. Both are either expanded or compressed, for example. This has the effect that both show a wavelength change in the same direction, namely two positive signals or two negative signals. It derives therefrom that a angling around the axis B has not occurred. Given this modification, the difference wavelength measuring is possible. As a result, it is possible to determine the angling of ball-and-socket joints in a simple manner, since each angle can be unambiguously acquired no matter in which direction—discrete pivot axes then no longer exist—due to the given four signals.

Figure 4:
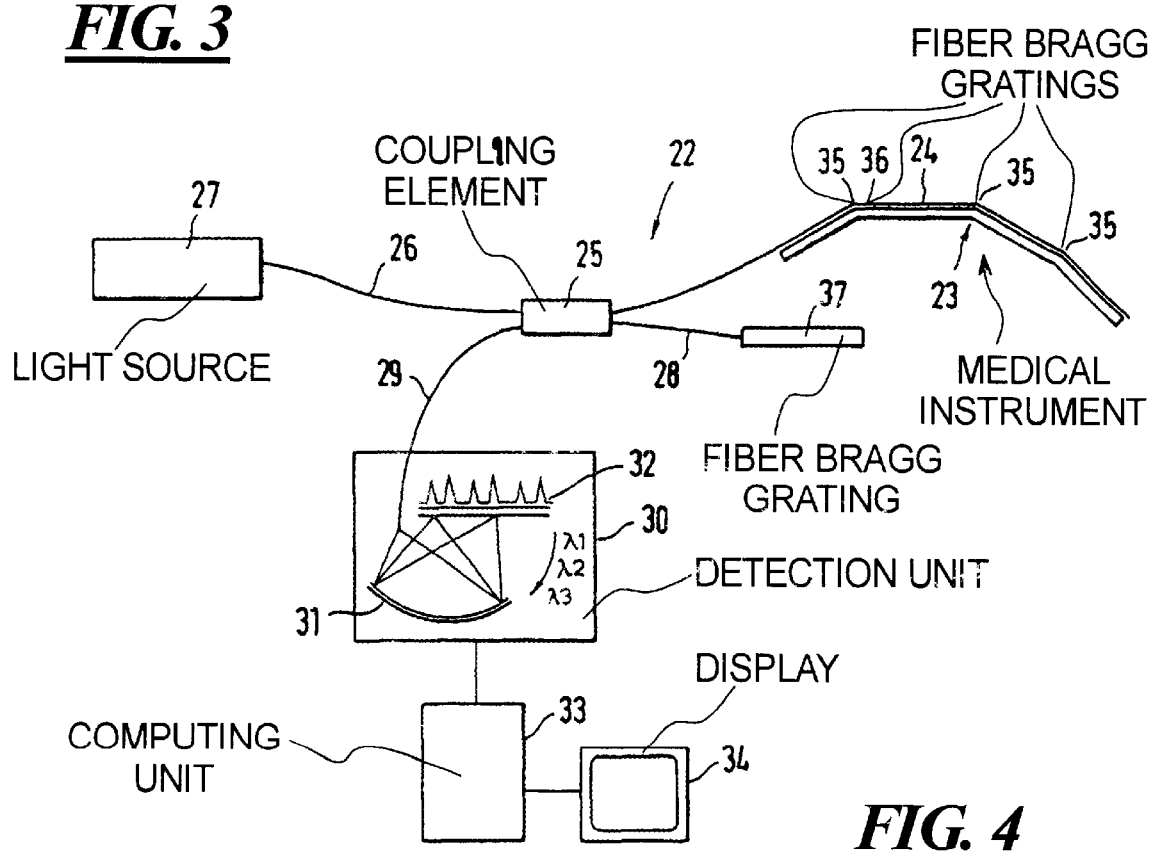
FIG. 4 is a schematic diagram of an inventive examination device or treatment device including the inventive optical navigation system.

In a schematic diagram, FIG. 4 shows an inventive examination or treatment device 22 having an inventive optical navigation system. The examination or treatment device 22 has a medical instrument 23 of the aforementioned type. The example only shows a optical fiber 24 having three fiber Bragg gratings 35 fashioned at three joint areas and a fiber Bragg grating 36 for the temperature compensation. Two or four conductors can be provided. The conductor 24 discharges into an optical coupling element 25, which is preferably fashioned as a plug, so that the instrument 23 can be decoupled. A optical fiber 26, via which light of a light source 27 is led and is inserted into the optical fiber 24, also discharges into the optical coupling element 25. The light source 27 can be a variable frequency laser diode or a LED, for example. Other light sources having a somewhat more broadband emission spectrum can be used. The light of the light source 27 supplied to the coupling element is divided in the coupling element 25 and is supplied to a reference optical fiber 28 with a separate fiber Bragg grating 37, which is encapsulated in the exemplary embodiment, and which is external relative to the instrument 23, for supplying a reference signal for calibrating purposes.

The light coupled into the optical fibers 24, 28 is reflected in a wavelength-sensitive fashion at the respective fiber-Bragg gratings. The reflected light of the different wavelengths is forwarded via a further optical fiber 29 to a detection unit 30. It can be fashioned as a spectrometer or interferometer. In the shown example, the detection unit is a polychromator 31 from where the incident light is thrown onto a CCD sensor 32, from which it is read out and the respective reflected light wavelengths (represented by λ1, λ2, λ3) can be determined.

The determined reflected light wavelengths are subsequently forwarded to a computing unit 33, in which the positions of the sections 2, on the basis of a corresponding calculating algorithm, are determined relative to one another and the position of the instrument 23 overall in the respective coordinate system of the navigation system. In order to determine the exact position, the geometric dimensions of the instrument 23 must be "known" by the computing unit 33, and a fixed coordinate zero point must be given. Given the instrument shown in FIG. 1, it can be situated in the connecting point at the arm 5.

In addition to the determination of the position of the instrument, the computing unit 33 is also fashioned for mixing the instrument 23 into a patient image of the treatment area shown at a display device 34 in the form of a monitor in a way providing the exact position. Since the patient image is picked up in a different coordinate system than that in which the position of the instrument 23 is normally determined, a coordinate transformation into the coordinate system of the patient image known to the computing unit 33 must be undertaken in the computing unit 33.

Instead of the combination LED-polychromator, a variable frequency laser diode generating light with an exactly determinable wavelength can also be utilized as a light source. This laser diode can be operated such that it sweeps a specific wavelength range, so that the broadband light is emitted in this way. A simple detector determining the Bragg-peaks can be used as a detector, since the chronological wavelength curve is exactly known.

Alternatively, a broadband light source and variable frequency filter (Fabry-Perot) following the light source can be used with which a chronological wavelength change also is achieved. A simple detector acquiring the reflection is also sufficient as a detector, since the peak can be allocated to a specific wavelength, which has been passed through the filter.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical instrument comprising:
   an elongratingd instrument body, adapted for insertion into an examination subject, having a plurality of successive rigid sections;
   a plurality of articulated joints respectively disposed between adjacent sections in said plurality of rigid sections, allowing said adjacent sections to be angled relative to each other; and
   at least one fiber optic light conductor, chargeable with light, disposed along said instrument body, said light conductor having at least one fiber Bragg grating therein in a region adjacent at least one of said articulated joints which is deformed to a degree corresponding to angling of the adjacent sections at said at least one of said articulated joints, thereby modulating said light in said light conductor.

2. A medical instrument as claimed in claim 1 wherein said light conductor has at least one further fiber Bragg grating, disposed at a non-deformable region of said light conductor, for producing an optical signal indicative of a temperature of said light conductor in said non-deformable region.

3. A medical instrument as claimed in claim 1 wherein said light conductor has a plurality of fiber Bragg gratings respectively disposed at regions of said light conductor which are respectively adjacent each of said articulated joints, and wherein each of said fiber Bragg gratings reflects light in a grating-specific wavelength range, with the respective wavelength ranges of said plurality of fiber Bragg gratings each being different.

4. A medical instrument as claimed in claim 3 wherein any two successive ones of said fiber Bragg gratings respectively reflect light at wavelengths which differ by at least 3 nm when said light conductor is not deformed.

5. A medical instrument as claimed in claim 3 wherein any two successive ones of said fiber Bragg gratings respectively reflect light at wavelengths which differ by at least 5 nm when said light conductor is not deformed.

6. A medical instrument as claimed in claim 3 wherein said light conductor comprises a plurality of further fiber Bragg gratings, disposed at respective, non-deformable regions of said light conductor, respectively allocated to said regions respectively adjacent said articulated joints, each of said further fiber Bragg gratings modulating said light dependent on a temperature of said light conductor in the non-deformable region of said light conductor in which that further fiber Bragg grating is disposed.

7. A medical instrument as claimed in claim 1 wherein said light conductor is a first light conductor, and wherein said medical instrument further comprises a second fiber optic light conductor, chargeable with light, disposed along said instrument body at a position offset by 90° relative to said first light conductor, said second light conductor having at least one fiber Bragg grating therein in a region of said second light conductor adjacent at least one of said articulated joints which is deformed to a degree corresponding to angling of the adjacent sections at said at least one of said articulated joints, thereby modulating said light in said second light conductor.

8. A medical instrument as claimed in claim 7 further comprising, in at least one of said first and second light conductors, at least one further fiber Bragg grating, disposed at a non-deformable region of said at least one of said conductors, for producing an optical signal indicative of a temperature of said one of said light conductors in said non-deformable region.

9. A medical instrument as claimed in claim 7 further comprising, in each of said first and second light conductors, at least one further fiber Bragg grating, disposed at a non-deformable region of the light conductor, for producing an optical signal indicative of a temperature of the light conductor in said non-deformable region.

10. A medical instrument as claimed in claim 7 wherein each of said first light conductor and said second light conductor has a plurality of fiber Bragg gratings respectively disposed at regions of the respective light conductor which are respectively adjacent each of said articulated joints, and wherein each of said fiber Bragg gratings in said first light conductor reflects light in a grating-specific wavelength range, with the respective wavelength ranges of said plurality of fiber Bragg gratings in said first light conductor each being different, and wherein each of said fiber Bragg gratings in said second light conductor reflects light in a grating-specific wavelength range, with the respective wavelength ranges of said plurality of said fiber Bragg gratings in said second light conductor being different.

11. A medical instrument as claimed in claim 9 wherein each of said first and second light conductors comprises a plurality of further fiber Bragg gratings, disposed at respective, non-deformable regions of the respective light conductor, respectively allocated to said regions respectively adjacent said articulated joints, said further fiber Bragg gratings in said first light conductor modulating said light dependent on a temperature of said first light conductor in the non-deformable region of the first light conductor in which that further Bragg grating is disposed, and each of said further fiber Bragg gratings in said second light conductor modulating said light dependent on a temperature of said second light conductor in the non-deformable region of said second light conductor in which that further fiber Bragg grating is disposed.

12. A medical instrument as claimed in claim 1 wherein said light conductor is a first light conductor, and wherein said medical instrument further comprises a second fiber optic light conductor, a third fiber optic light conductor, and a fourth fiber optic light conductor, each chargeable with light, disposed along said instrument body at respective positions offset by 90°, and wherein each of said first, second, third and fourth conductors has at least one fiber Bragg grating therein in a region of the respective conductor adjacent at least one of said articulated joints which is deformed to a degree corresponding to angling of the adjacent sections at said at least one of said articulated joints, thereby modulating said light in the respective light conductor.

13. A medical instrument as claimed in claim 12 comprising, in at least one of said first, second, third and fourth light conductors, at least one further fiber Bragg grating, disposed at a non-deformable region of the respective light conductor, for producing an optical signal indicative of a temperature of the respective light conductor in said non-deformable region.

14. A medical instrument as claimed in claim 13 wherein each of said first, second, third and fourth light conductors has a plurality of fiber Bragg gratings respectively disposed at regions of the respective light conductor which are respectively adjacent each of said articulated joints, and wherein each of said fiber Bragg gratings in said first light conductor reflects light in a grating-specific wavelength range, with the respective wavelength ranges of said plurality of fiber Bragg gratings in said first light conductor each being different, and wherein each of said fiber Bragg gratings in said second light conductor reflects light in a grating-specific wavelength range, with the respective wavelength ranges of said plurality of fiber Bragg gratings in said second light conductor being different, and wherein each of said fiber Bragg gratings in said third light conductor reflects light in a grating-specific wavelength range, with the respective wavelength ranges of said plurality of fiber Bragg gratings in said third light conductor each being different, and wherein each of said fiber Bragg gratings in said fourth light conductor reflects light in a grating-specific wavelength range, with the respective wavelength ranges of said plurality of fiber Bragg gratings in said fourth light conductor each being different.

15. A medical instrument as claimed in claim 14 wherein each of said first, second, third and fourth light conductors comprises a plurality of further fiber Bragg gratings, disposed at respective, non-deformable regions of the respective light conductor, respectively allocated to said regions in the respective light conductor respectively adjacent said articulated joints, each of said further fiber Bragg gratings in said first light conductor modulating said light dependent on a temperature of said first light conductor in the non-deformable region of said first light conductor in which that further fiber Bragg grating is disposed, each of said further fiber Bragg gratings in said second light conductor modulating said light dependent on a temperature of said second light conductor in the non-deformable region of said second light conductor in which that further fiber Bragg grating is disposed, each of said further fiber Bragg gratings in said third light conductor modulating said light dependent on a temperature of said third light conductor in the non-deformable region of said third light conductor in which that further fiber Bragg grating is disposed, and each of said further fiber Bragg gratings in said fourth light conductor modulating said light dependent on a temperature of said fourth light conductor in the non-deformable region of said fourth light conductor in which that further fiber Bragg grating is disposed.

16. A medical instrument as claimed in claim 1 wherein said at least one fiber Bragg grating is sensitive to wavelengths of said light in a range selected from the group of ranges consisting of a range between 750 nm to 850 nm, a range 1250 nm to 1350 nm, and a range between 1500 nm to 1600 nm.

17. A medical examination/treatment device comprising:
a medical instrument having an elongated instrument body, adapted for insertion into an examination subject, having a plurality of successive rigid sections;
a plurality of articulated joints respectively disposed between adjacent sections in said plurality of rigid sections, allowing said adjacent sections to be angled relative to each other;
a light source;
at least one fiber optic light conductor, couplable to said light source and chargeable with light from said light source, disposed along said instrument body, said light conductor having at least one fiber Bragg grating therein in a region adjacent at least one of said articulated joints which is deformed to a degree corresponding to angling of the adjacent sections at said at least one of said articulated joints, thereby modulating a wavelength of said light in said light conductor; and
a detection unit couplable to said at least one light conductor, for receiving the modulated light from said at least one light conductor and for determining an angular position of said adjacent sections, and thus a position of said medical instrument, from said modulated light.

18. A medical examination/treatment device as claimed in claim 17 wherein said light source emits light with a spectral bandwidth of 10 nm to 60 nm.

19. A medical examination/treatment device as claimed in claim 17 wherein said light source is a variable frequency laser diode.

20. A medical examination/treatment device as claimed in claim 17 wherein said light source is a light-emitting diode.

21. A medical examination/treatment device as claimed in claim 17 further comprising a reference light conductor having a reference fiber Bragg grating, said reference light waveguide being optically couplable to said light source and optically couplable to said detection unit for supplying an optical reference signal to said detection unit.

22. A medical examination/treatment device as claimed in claim 17 wherein said detection unit is a spectrometer.

23. A medical examination/treatment device as claimed in claim 17 wherein said detection unit is an interferometer.

24. A medical examination/treatment device as claimed in claim 17 further comprising a display unit connected to said detection unit for displaying an image of said examination subject with a representation of said spatial position of said medical instrument mixed into said image.

25. A medical examination/treatment device as claimed in claim 17 wherein said light conductor has at least one further fiber Bragg grating, disposed at a non-deformable region of said light conductor, for producing an optical signal indicative of a temperature of said light conductor in said non-deformable region.

26. A medical examination/treatment device as claimed in claim 17 wherein said light conductor has a plurality of fiber Bragg gratings respectively disposed at regions of said light conductor which are respectively adjacent each of said articulated joints, and wherein each of said fiber Bragg gratings reflects light in a grating-specific wavelength range, with the respective wavelength ranges of said plurality of fiber Bragg gratings each being different.

27. A medical examination/treatment device as claimed in claim 26 wherein any two successive ones of said fiber Bragg gratings respectively reflect light at wavelengths which differ by at least 3 nm when said light conductor is not deformed.

28. A medical examination/treatment device as claimed in claim 26 wherein any two successive ones of said fiber Bragg gratings respectively reflect light at wavelengths which differ by at least 5 nm when said light conductor is not deformed.

29. A medical examination/treatment device as claimed in claim 26 wherein said light conductor comprises a plurality of further fiber Bragg gratings, disposed at respective, non-deformable regions of said light conductor, respectively allocated to said regions respectively adjacent said articulated joints, each of said further fiber Bragg gratings modulating said light dependent on a temperature of said light conductor in the non-deformable region of said light conductor in which that further fiber Bragg grating is disposed.

30. A medical examination/treatment device as claimed in claim 17 wherein said light conductor is a first light conductor, and wherein said medical instrument further comprises a second fiber optic light conductor, chargeable with light, disposed along said instrument body at a position offset by 90° relative to said first light conductor, said second light conductor having at least one fiber Bragg grating therein in a region of said second light conductor adjacent at least one of said articulated joints which is deformed to a degree corresponding to angling of the adjacent sections at said at least one of said articulated joints, thereby modulating said light in said second light conductor.

31. A medical examination/treatment device as claimed in claim 30 further comprising, in at least one of said first and second light conductors, at least one further fiber Bragg grating, disposed at a non-deformable region of said at least one of said conductors, for producing an optical signal indicative of a temperature of said one of said light conductors in said non-deformable region.

32. A medical examination/treatment device as claimed in claim 30 further comprising, in each of said first and second light conductors, at least one further fiber Bragg grating, disposed at a non-deformable region of the light conductor, for producing an optical signal indicative of a temperature of the light conductor in said non-deformable region.

33. A medical examination/treatment device as claimed in claim 30 wherein each of said first light conductor and said second light conductor has a plurality of fiber Bragg gratings respectively disposed at regions of the respective light conductor which are respectively adjacent each of said articulated joints, and wherein each of said fiber Bragg gratings in said first light conductor reflects light in a grating-specific wavelength range, with the respective wavelength ranges of said plurality of fiber Bragg gratings in said first light conductor each being different, and wherein each of said fiber Bragg gratings in said second light conductor reflects light in a grating-specific wavelength range, with the respective wavelength ranges of said plurality of said fiber Bragg gratings in said second light conductor being different.

34. A medical examination/treatment device as claimed in claim 33 wherein each of said first and second light conductors comprises a plurality of further fiber Bragg gratings, disposed at respective, non-deformable regions of the respective light conductor, respectively allocated to said regions respectively adjacent said articulated joints, said further fiber Bragg gratings in said first light conductor modulating said light dependent on a temperature of said first light conductor in the non-deformable region of the first light conductor in which that further Bragg grating is disposed, and each of said further fiber Bragg gratings in said second light conductor modulating said light dependent on a temperature of said second light conductor in the non-deformable region of said second light conductor in which that further fiber Bragg grating is disposed.

35. A medical examination/treatment device as claimed in claim 17 wherein said light conductor is a first light conductor, and wherein said medical instrument further comprises a second fiber optic light conductor, a third fiber optic light conductor, and a fourth fiber optic light conductor, each chargeable with light, disposed along said instrument body at respective positions offset by 90°, and wherein each of said first, second, third and fourth conductors has at least one fiber Bragg grating therein in a region of the respective conductor adjacent at least one of said articulated joints which is deformed to a degree corresponding to angling of the adjacent sections at said at least one of said articulated joints, thereby modulating said light in the respective light conductor.

36. A medical examination/treatment device as claimed in claim 35 comprising, in at least one of said first, second, third and fourth light conductors, at least one further fiber Bragg grating, disposed at a non-deformable region of the respective light conductor, for producing an optical signal indicative of a temperature of the respective light conductor in said non-deformable region.

37. A medical examination/treatment device as claimed in claim 35 wherein each of said first, second, third and fourth light conductors has a plurality of fiber Bragg gratings respectively disposed at regions of the respective light conductor which are respectively adjacent each of said articulated joints, and wherein each of said fiber Bragg gratings in said first light conductor reflects light in a grating-specific wavelength range, with the respective wavelength ranges of said plurality of fiber Bragg gratings in said first light conductor each being different, and wherein each of said fiber Bragg gratings in said second light conductor reflects light in a grating-specific wavelength range, with the respective wavelength ranges of said plurality of fiber Bragg gratings in said second light conductor being different, and wherein each of said fiber Bragg gratings in said third light conductor reflects light in a grating-specific wavelength range, with the respective wavelength ranges of said plurality of fiber Bragg gratings in said third light conductor each being different, and wherein each of said fiber Bragg gratings in said fourth light conductor reflects light in a grating-specific wavelength range, with the respective wavelength ranges of said plurality of fiber Bragg gratings in said fourth light conductor each being different.

38. A medical examination/treatment device as claimed in claim 37 wherein each of said first, second, third and fourth light conductors comprises a plurality of further fiber Bragg gratings, disposed at respective, non-deformable regions of the respective light conductor, respectively allocated to said regions in the respective light conductor respectively adjacent said articulated joints, each of said further fiber Bragg gratings in said first light conductor modulating said light dependent on a temperature of said first light conductor in the non-deformable region of said first light conductor in which that further fiber Bragg grating is disposed, each of said further fiber Bragg gratings in said second light conductor modulating said light dependent on a temperature of said second light conductor in the non-deformable region of said second light conductor in which that further fiber Bragg grating is disposed, each of said further fiber Bragg gratings in said third light conductor modulating said light dependent on a temperature of said third light conductor in the non-deformable region of said third light conductor in which that further fiber Bragg grating is disposed, and each of said further fiber Bragg gratings in said fourth light conductor modulating said light dependent on a temperature of said fourth light conductor in the non-deformable region of said fourth light conductor in which that further fiber Bragg grating is disposed.

39. A medical examination/treatment device as claimed in claim 17 wherein said at least one fiber Bragg grating is sensitive to wavelengths of said light in a range selected from the group of ranges consisting of a range between 750 nm to 850 nm, a range 1250 nm to 1350 nm, and a range between 1500 nm to 1600 nm.

40. An optical navigation system comprising:
  a medical instrument having an elongated instrument body, adapted for insertion into an examination subject, having a plurality of successive rigid sections;
  a plurality of articulated joints respectively disposed between adjacent sections in said plurality of rigid sections, allowing said adjacent sections to be angled relative to each other;
  a light source;
  at least one fiber optic light conductor, couplable to said light source and chargeable with light from said light source, disposed along said instrument body, said light conductor having at least one fiber Bragg grating therein in a region adjacent at least one of said articulated joints which is deformed to a degree corresponding to angling of the adjacent sections at said at least one of said articulated joints, thereby modulating a wavelength of said light in said light conductor;
  a detection unit couplable to said at least one light conductor, for detecting the modulated light from said at least one light conductor; and
  a computer unit, connected to said detector unit, for determining an angular position of said adjacent sections, and thus a position of said medical instrument, from said modulated light detected by said detector unit.

41. An optical navigation system as claimed in claim 40 wherein said light source emits light with a spectral bandwidth of 10 nm to 60 nm.

42. An optical navigation system as claimed in claim 40 wherein said light source is a variable frequency laser diode.

43. An optical navigation system as claimed in claim 40 wherein said light source is a light-emitting diode.

44. An optical navigation system as claimed in claim 40 further comprising a reference light conductor having a reference fiber Bragg grating, said reference light waveguide being optically couplable to said light source and optically couplable to said detection unit for supplying an optical reference signal to said detection unit.

45. An optical navigation system as claimed in claim 40 wherein said detection unit is a spectrometer.

46. An optical navigation system as claimed in claim 40 wherein said detection unit is an interferometer.

47. An optical navigation system as claimed in claim 40 further comprising a display unit connected to said computer unit for displaying an image of said examination subject with a representation of said spatial position of said medical instrument mixed into said image.

48. An optical navigation system as claimed in claim 40 wherein said light conductor has at least one further fiber Bragg grating, disposed at a non-deformable region of said light conductor, for producing an optical signal indicative of a temperature of said light conductor in said non-deformable region.

49. An optical navigation system as claimed in claim 40 wherein said light conductor has a plurality of fiber Bragg gratings respectively disposed at regions of said light conductor which are respectively adjacent each of said articulated joints, and wherein each of said fiber Bragg gratings reflects light in a grating-specific wavelength range, with the respective wavelength ranges of said plurality of fiber Bragg gratings each being different.

50. An optical navigation system as claimed in claim 49 wherein any two successive ones of said fiber Bragg gratings respectively reflect light at wavelengths which differ by at least 3 nm when said light conductor is not deformed.

51. An optical navigation system as claimed in claim 49 wherein any two successive ones of said fiber Bragg gratings respectively reflect light at wavelengths which differ by at least 5 nm when said light conductor is not deformed.

52. An optical navigation system as claimed in claim 49 wherein said light conductor comprises a plurality of further fiber Bragg gratings, disposed at respective, non-deformable regions of said light conductor, respectively allocated to said regions respectively adjacent said articulated joints, each of said further fiber Bragg gratings modulating said light dependent on a temperature of said light conductor in the non-deformable region of said light conductor in which that further fiber Bragg grating is disposed.

53. An optical navigation system as claimed in claim 40 wherein said light conductor is a first light conductor, and wherein said medical instrument further comprises a second fiber optic light conductor, chargeable with light, disposed along said instrument body at a position offset by 90° relative to said first light conductor, said second light conductor having at least one fiber Bragg grating therein in a region of said second light conductor adjacent at least one of said articulated joints which is deformed to a degree corresponding to angling of the adjacent sections at said at least one of said articulated joints, thereby modulating said light in said second light conductor.

54. An optical navigation system as claimed in claim 53 further comprising, in at least one of said first and second light conductors, at least one further fiber Bragg grating, disposed at a non-deformable region of said at least one of said conductors, for producing an optical signal indicative of a temperature of said one of said light conductors in said non-deformable region.

55. An optical navigation system as claimed in claim 53 further comprising, in each of said first and second light conductors, at least one further fiber Bragg grating, disposed at a non-deformable region of the light conductor, for producing an optical signal indicative of a temperature of the light conductor in said non-deformable region.

56. An optical navigation system as claimed in claim 53 wherein each of said first light conductor and said second light conductor has a plurality of fiber Bragg gratings respectively disposed at regions of the respective light conductor which are respectively adjacent each of said articulated joints, and wherein each of said fiber Bragg gratings in said first light conductor reflects light in a grating-specific wavelength range, with the respective wavelength ranges of said plurality of fiber Bragg gratings in said first light conductor each being different, and wherein each of said fiber Bragg gratings in said second light conductor reflects light in a grating-specific wavelength range, with the respective wavelength ranges of said plurality of said fiber Bragg gratings in said second light conductor being different.

57. An optical navigation system as claimed in claim 56 wherein each of said first and second light conductors comprises a plurality of further fiber Bragg gratings, disposed at respective, non-deformable regions of the respective light conductor, respectively allocated to said regions respectively adjacent said articulated joints, said further fiber Bragg gratings in said first light conductor modulating said light dependent on a temperature of said first light conductor in the non-deformable region of the first light conductor in which that further Bragg grating is disposed, and each of said further fiber Bragg gratings in said second light conductor modulating said light dependent on a temperature of said second light conductor in the non-deformable region of said second light conductor in which that further fiber Bragg grating is disposed.

58. An optical navigation system as claimed in claim 40 wherein said light conductor is a first light conductor, and wherein said medical instrument further comprises a second fiber optic light conductor, a third fiber optic light conductor, and a fourth fiber optic light conductor, each chargeable with light, disposed along said instrument body at respective positions offset by 90°, and wherein each of said first, second, third and fourth conductors has at least one fiber Bragg grating therein in a region of the respective conductor adjacent at least one of said articulated joints which is deformed to a degree corresponding to angling of the adjacent sections at said at least one of said articulated joints, thereby modulating said light in the respective light conductor.

59. An optical navigation system as claimed in claim 58 comprising, in at least one of said first, second, third and fourth light conductors, at least one further fiber Bragg grating, disposed at a non-deformable region of the respective light conductor, for producing an optical signal indicative of a temperature of the respective light conductor in said non-deformable region.

60. An optical navigation system as claimed in claim 58 wherein each of said first, second, third and fourth light conductors has a plurality of fiber Bragg gratings respectively disposed at regions of the respective light conductor which are respectively adjacent each of said articulated joints, and wherein each of said fiber Bragg gratings in said first light conductor reflects light in a grating-specific wavelength range, with the respective wavelength ranges of said plurality of fiber Bragg gratings in said first light conductor each being different, and wherein each of said fiber Bragg gratings in said second light conductor reflects light in a grating-specific wavelength range, with the respective wavelength ranges of said plurality of fiber Bragg gratings in said second light conductor being different, and wherein each of said fiber Bragg gratings in said third light conductor reflects light in a grating-specific wavelength range, with the respective wavelength ranges of said plurality of fiber Bragg gratings in said third light conductor each being different, and wherein each of said fiber Bragg gratings in said fourth light conductor reflects light in a grating-specific wavelength range, with the respective wavelength ranges of said plurality of fiber Bragg gratings in said fourth light conductor each being different.

61. An optical navigation system as claimed in claim 60 wherein each of said first, second, third and fourth light conductors comprises a plurality of further fiber Bragg gratings, disposed at respective, non-deformable regions of the respective light conductor, respectively allocated to said regions in the respective light conductor respectively adjacent said articulated joints, each of said further fiber Bragg gratings in said first light conductor modulating said light dependent on a temperature of said first light conductor in the non-deformable region of said first light conductor in which that further fiber Bragg grating is disposed, each of said further fiber Bragg gratings in said second light conductor modulating said light dependent on a temperature of said second light conductor in the non-deformable region of said second light conductor in which that further fiber Bragg grating is disposed, each of said further fiber Bragg gratings in said third light conductor modulating said light dependent on a temperature of said third light conductor in the non-deformable region of said third light conductor in which that further fiber Bragg grating is disposed, and each of said further fiber Bragg gratings in said fourth light conductor modulating said light dependent on a temperature of said fourth light conductor in the non-deformable region of said fourth light conductor in which that further fiber Bragg grating is disposed.

62. An optical navigation system as claimed in claim 40 wherein said at least one fiber Bragg grating is sensitive to wavelengths of said light in a range selected from the group of ranges consisting of a range between 750 nm to 850 nm, a range 1250 nm to 1350 nm, and a range between 1500 nm to 1600 nm.

* * * * *